United States Patent [19]

Bridges et al.

[11] Patent Number: 4,780,468

[45] Date of Patent: Oct. 25, 1988

[54] 8-TRIFLUOROMETHYL QUINOLONES AS ANTIBACTERIAL AGENTS

[75] Inventors: Alexander J. Bridges, Ann Arbor; John M. Domagala, Canton, both of Mich.

[73] Assignee: Warner-Lambert Company, Morris Plains, N.J.

[21] Appl. No.: 83,532

[22] Filed: Aug. 7, 1987

[51] Int. Cl.$^4$ .................. C07D 401/04; C07D 451/02; C07D 451/04; A61K 31/47

[52] U.S. Cl. .................................... 514/312; 514/210; 514/215; 514/249; 514/255; 514/278; 514/304; 540/580; 544/349; 544/351; 544/363; 546/15; 546/16; 546/126; 546/156; 560/38; 560/51; 562/493; 570/127; 570/182

[58] Field of Search ................... 546/15, 16, 126, 156; 514/210, 278, 312, 304

[56] References Cited

U.S. PATENT DOCUMENTS

| 4,571,396 | 2/1986 | Hutt et al. | 546/126 |
| 4,665,079 | 5/1987 | Culbertson et al. | 546/156 |

FOREIGN PATENT DOCUMENTS

| 172651 | 2/1986 | European Pat. Off. |
| 0172004 | 2/1986 | European Pat. Off. |
| 830832 | 3/1960 | United Kingdom |

Primary Examiner—Donald G. Daus
Assistant Examiner—E. Bernhardt
Attorney, Agent, or Firm—Elizabeth M. Anderson

[57] ABSTRACT

A novel series of quinolone carboxylic acids for use as antibacterial agents are described. Methods for making the compounds, methods of using the compounds and compositions containing them are also described. Certain novel intermediates are also described.

18 Claims, No Drawings

8-TRIFLUOROMETHYL QUINOLONES AS ANTIBACTERIAL AGENTS

BACKGROUND OF THE INVENTION

U.S. Pat. No. 4,341,784 discloses certain substituted 7-(3-amino-1-pyrrolidinyl)-1-ethyl-6-fluoro-1,4-dihydro-4-oxo-1,8-naphthyridine-3-carboxylic acids having the general formula:

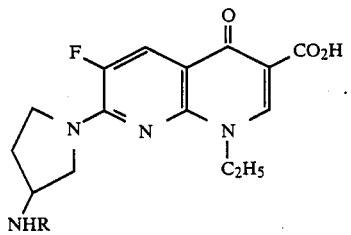

The Journal of Medicinal Chemistry, 23, 1358 (1980) discloses certain substituted 3-quinolinecarboxylic acids having the structural formula

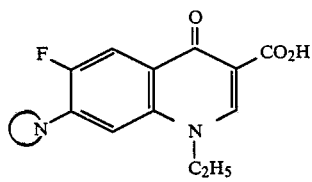

wherein

may be pyrrolidinyl. See also U.S. Pat. No. 4,146,719.

Certain 7-heterocyclic substituted 1,8-naphthyridines are disclosed in Eur. J. Med. Chem.—Chimica Therapeutica, 29, 27 (1977). U.S. Pat. Nos. 3,753,993, 3,907,808, and U.S. Pat. No 4,604,401 disclose certain 7-pyridylquinolines.

European Application No. 184,384 discloses certain substituted dihydroquinoline derivatives having the formula

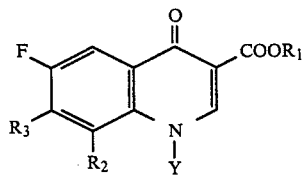

wherein in part $R_1$ is hydrogen, 1-6C alkyl, benzyl, or a pharmaceutically acceptable cation; $R_2$ may be hydrogen or fluorine; $R_3$ an optionally substituted phenyl; and Y optionally substituted 1-3C alkyl, hydroxyethyl, cyclopropyl, vinyl, allyl or phenyl.

The references teach that these compounds possesses antibacterial activity.

SUMMARY

One aspect of the present invention is a compound of formula

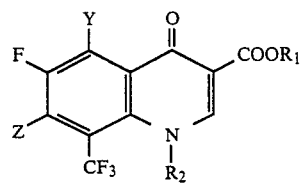

wherein
$R_1$ is hydrogen, an alkyl of from one to six carbon atoms or a cation;
$R_2$ is alkyl of from one to four carbon atoms, vinyl, haloalkyl or hydroxyalkyl of from one to four carbon atoms or cycloalkyl of from three to six carbon atoms;
Y is hydrogen, fluoro or amino;
Z is

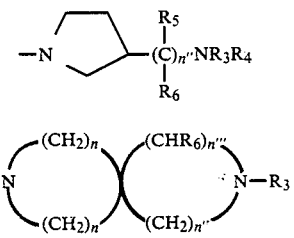

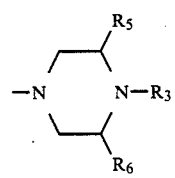

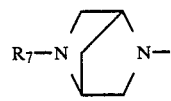

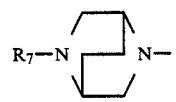

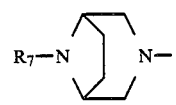

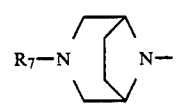

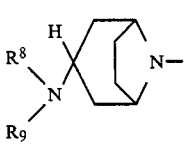

-continued

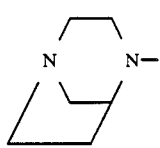

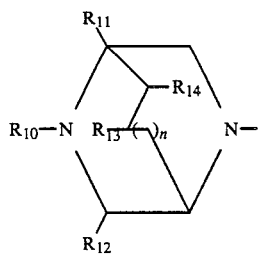

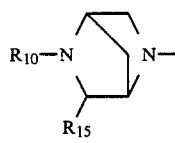

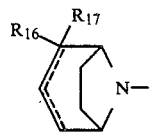

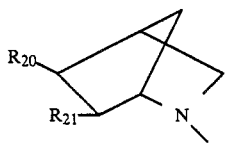

wherein
n is 1, 2, 3, or 4;
n' is 1, 2, 3, or 4;
n+n' is a total of 2, 3, 4, or 5;
n" is 0, 1, or 2;
n'" is 0, 1, or 2;
n$^{Iv}$ is 1, 2, or 3;
n$^v$ is 0 or 1;
$R_3$ is hydrogen, alkyl of from one to four carbon atoms or a cycloalkyl of from three to six carbon atoms;
$R_4$ is hydrogen, alkyl of from one to four carbon atoms, hydroxyalkyl of from two or four carbon atoms, trifluoroethyl, or $R_4'CO$ wherein $R_4'$ is alkyl of from one to four carbon atoms, or alkoxy of from one to four carbon atoms;
$R_5$ and $R_6$ are each independently hydrogen or alkyl of from one to three carbon atoms;
$R_7$ is hydrogen, alkyl of from one to three carbon atoms, hydroxyalkyl of from two to three carbon atoms, benzyl, or p-aminobenzyl;
$R_8$ and $R_9$ are each independently hydrogen, alkanoyl of from one to three carbon atoms, alkyl of from one to three carbon atoms, isopropyl or cyclopropyl;
$R_{10}$ and $R_{11}$ are each independently hydrogen, methyl, ethyl, or benzyl;
$R_{12}$, $R_{13}$, and $R_{14}$ are each independently hydrogen or methyl;
$R_{15}$ is methyl, ethyl, or isopropyl;

$R_{16}$ is $CH_2OR_{18}$, $CH_2NR_{18}R_{19}$, or $NR_{18}R_{19}$ wherein $R_{18}$ and $R_{19}$ are hydrogen, alkyl of from one to three carbon atoms, acyl of from one to three carbon atoms;
$R_{17}$ is absent, hydrogen or alkyl of from one to three carbon atoms;
wherein the dotted line means a single or double bond;
$R_{20}$ and $R_{21}$ are each independently hydrogen, halogen, $NR_{22}R_{23}$, $OR_{22}$, $SR_{22}$, alkyl of from one to three carbon atoms, wherein $R_{22}$ and $R_{23}$ are each independently hydrogen, alkyl of from one to three carbon atoms, or acyl of from one to three carbon atoms;
or a pharmaceutically acceptable acid addition or base salt thereof.

The preferred compounds of this invention are those wherein $R_2$ is ethyl, vinyl, 2-fluoroethyl, difluoroethyl, or cyclopropyl.

Also preferred compounds of this invention are those wherein Z is

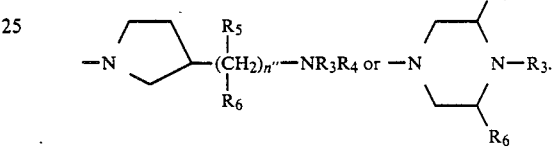

Other preferred compounds of this invention are those wherein $R_1$ is hydrogen or a pharmaceutically acceptable base salt such as a metal or an amine salt.

Other preferred compounds of this invention are those wherein n" is one, $R_3$, $R_5$, and $R_6$ are hydrogen, mewthyl, ethyl, or n-propyl, and $R_4$ is hydrogen.

The most preferred compounds are those wherein Z is

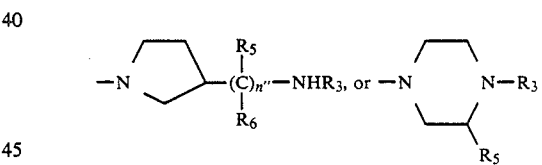

wherein $R_1$ is hydrogen; $R_2$ is ethyl, vinyl, 2-fluoroethyl, or cyclopropyl; and $R_3$ is hydrogen, methyl, ethyl, 1-propyl, 2-propyl, $R_5$ and $R_6$ are hydrogen or methyl, or a pharmaceutically acceptable acid addition or base salt thereof.

Additionally the most preferred compounds include those wherein $R_2$ is cyclopropyl, Z is

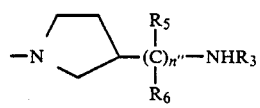

in which n" is 0 or 1 and $R_3$ is hydrogen, methyl, ethyl, 1-propyl, 2-propyl, $R_5$ and $R_6$ are hydrogen or methyl, and R is hydrogen or a pharmaceutically acceptable base salt thereof. Particularly preferred species of the invention are those compounds having the names:
7-(3-(aminomethyl)pyrrolidin-1-yl)-1-ethyl-6-fluoro-8-trifluoromethyl-1,4-dihydro-4-oxo-quinoline-3-carboxylic acid, 7-[3-(1-aminoethyl)-1-pyrrolidinyl]-1-cyclopropyl-6-fluoro-1,4-dihydro-4-oxo-8-(trifluoromethyl)-3-quinolinecarboxylic acid,
1-cyclopropyl-7-3-[1-(ethylamino)ethyl]-1-pyrrolidinyl]-6-fluoro-1,4-dihydro-4-oxo-8-(trifluoromethyl)-3-quinolinecarboxylic acid,
1-cyclopropyl-6-fluoro-1,4-dihydro-7-[3-[1-methyl-1-(methylamino)ethyl]-1-pyrrolidinyl]-4-oxo-8-(trifluoromethyl)-3-quinolinecarboxylic acid,
7-[3-(aminomethyl)-1-pyrrolidinyl]-1-cyclopropyl-6-fluoro-1,4-dihydro-4-oxo-8-(trifluoromethyl)-3-quinolinecarboxylic acid,
1-ethyl-6-fluoro-1,4-dihydro-7-[3-[(methylamino)methyl]-1-pyrrolidinyl]-4-oxo-8-(trifluoromethyl)-3-quinolinecarboxylic acid,
1-cyclopropyl-6-fluoro-1,4-dihydro-7-[3-[(methylamino)methyl]-1-pyrrolidinyl]-4-oxo-8-(trifluoromethyl)-3-quinolinecarboxylic acid,
1-ethyl-7-[3-[(ethylamino)methyl]-1-pyrrolidinyl]-6-fluoro-1,4-dihydro-4-oxo-8-(trifluoromethyl)-3-quinolinecarboxylic acid,
1-cyclopropyl-7-[3-[(ethylamino)methyl]-1-pyrrolidinyl]-6-fluoro-1,4-dihydro-4-oxo-8-(trifluoromethyl)-3-quinolinecarboxylic acid,
1-ethyl-6-fluoro-1,4-dihydro-4-oxo-7-(1-piperazinyl)-8-(trifluoromethyl)-3-quinolinecarboxylic acid,
1-cyclopropyl-6-fluoro-1,4-dihydro-4-oxo-7-(1-piperazinyl)-8-(trifluoromethyl)-3-quinolinecarboxylic acid,
1-ethyl-6-fluoro-1,4-dihydro-7-(4-methyl-1-piperazinyl)-4-oxo-8-(trifluoromethyl)-3-quinolinecarboxylic acid,
1-cyclopropyl-6-fluoro-1,4-dihydro-7-(4-methyl-1-piperazinyl)-4-oxo-8-(trifluoromethyl)-3-quinolinecarboxylic acid,
1-cyclopropyl-6-fluoro-1,4-dihydro-7-(3-methyl-1-piperazinyl)-4-oxo-8-(trifluoromethyl)-3-quinolinecarboxylic acid,
7-(3-amino-1-pyrrolidinyl)-1-ethyl-6-fluoro-1,4-dihydro-4-oxo-8-(trifluoromethyl)-3-quinolinecarboxylic acid,
7-(3-amino-1-pyrrolidinyl)-1-cyclopropyl-6-fluoro-1,4-dihydro-4-oxo-8-(trifluoromethyl)-3-quinolinecarboxylic acid, and
7-[3-(1-amino-1-methylethyl)-1-pyrrolidinyl]-1-cyclopropyl-6-fluoro-1,4-dihydro-4-oxo-8-(trifluoromethyl)-3-quinolinecarboxylic acid.

Another aspect of the present invention is a novel process for preparing compounds of formula I

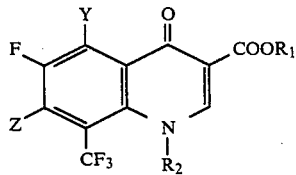

wherein Z, Y, $R_1$, and $R_2$ are as defined above. The process is fully described hereinafter.

Certain novel intermediates of the process are also included in the present invention. They include:
3-bromo-2,5,6-trifluorobenzoic acid,
1-bromo-2,4,5-trifluoro-3-(trifluoromethyl) benzene,
2,4,5-trifluoro-3-(trifluoromethyl)benzoic acid,
ethyl 2,4,5-trifluoro-β-oxo-3-(trifluoromethyl)benzenepropanoate,
1-cyclopropyl-6,7-difluoro-1,4-dihydro-4-oxo-8-(trifluoromethyl)-3-quinolinecarboxylic acid, ethyl ester, or
ethyl 1-cyclopropyl-6,7-difluoro-1,4-dihydro-4-oxo-8-(trifluoromethyl)-3-quinolinecarboxylate.

The invention also includes a pharmaceutical composition which comprises an antibacterially effective amount of a compound of formula I or a pharmaceutically acceptable salt thereof in combination with a pharmaceutically acceptable carrier.

The invention further includes a method for treating bacterial infections in a mammal which comprises administering an antibacterially effective amount of the above defined pharmaceutical composition to a mammal in need thereof.

DETAILED DESCRIPTION

The compounds of the invention having the formula

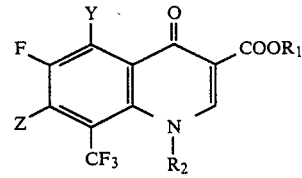

wherein the substituents are as defined above are capable of forming both pharmaceutically acceptable acid addition and/or base salts. Base salts are formed with metals or amines, such as alkali and alkaline earth metals or organic amines. Examples of metals used as cations are sodium, potassium, magnesium, calcium, and the like. Also included are heavy metal salts such as for example silver, zinc, cobalt, and cerium. Such heavy metal salts are effective in the treatment of burns especially when applied to the affected surface of a burn victim either directly or in combination with a physiologically acceptable carrier such as a water dispersible, hydrophilic carrier. Examples of suitable amines are N,N'-dibenzylethylenediamine, chloroprocaine, choline, diethanolamine, ethylenediamine, N-methylglucamine, and procaine.

Pharmaceutically acceptable acid addition salts are formed with organic and inorganic acids.

Examples of suitable acids for salt formation are hydrochloric, sulfuric, phosphoric, acetic, lactic, citric, oxalic, malonic, salicylic, malic, gluconic, fumaric, succinic, ascorbic, maleic, methanesulfonic, and the like. The salts are prepared by contacting the free base form with a sufficient amount of the desired acid to produce either a mono or di, etc salt in the conventional manner. The free base forms may be regenerated by treating the salt form with a base. For example, dilute solutions of aqueous base may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention. Use of excess base where R' is hydrogen gives the corresponding basic salt.

The compounds of the invention can exist in unsolvated as well as solvated forms, including hydrated forms. In general, the solvated forms, including hydrated forms and the like are equivalent to the unsolvated forms for purposes of the invention.

The alkyl groups contemplated by the invention comprise both straight and branched carbon chains of from one to about four carbon atoms except when specifically stated to be greater than four carbon atoms. Representative of such groups are methyl, ethyl, propyl, isopropyl, and the like.

The cycloalkyl groups contemplated by the invention comprise those having three to six carbon atoms such as cyclopropyl, cyclobutyl, cyclopentyl, and cyclohexyl.

The term alkanoyl is intended to

groups wherein $R^1$ is an alkyl of from one to three carbon atoms.

The hydroxyalkyl groups contemplated by the invention comprise those having two to four carbon atoms such as 2-hydroxyethyl, 2- or 3-hydroxypropyl, or 2-, 3-, or 4-hydroxybutyl.

The alkoxy groups contemplated by the invention comprise both straight and branched carbon chains of from one to about six carbon atoms unless otherwise specified. Representative of such groups are methoxy, ethoxy, propoxy, i-propoxy, t-butoxy, hexoxy, and the like.

The term, haloalkyl, is intended to include halogen substituted straight and branched carbon chains of from two to four carbon atoms. Those skilled in the art will recognize that the halogen substituent may not be present on the α-carbon atom of the chain. Representative of such groups are β-fluoroethyl, β-chloroethyl, β,β-dichloroethyl, β-chloropropyl, β-chloro-2-propyl, -iodobutyl, and the like.

The term halogen is intended to include fluorine, chlorine, bromine, and iodine unless otherwise specified.

Certain compounds of the invention may exist in optically active forms. The pure D isomer, pure L isomer as well as mixtures thereof; including the racemic mixtures, are contemplated by the invention. Additional asymmetric carbon atoms may be present in a substituent such as an alkyl group. All such isomers as well as mixtures thereof are intended to be included in the invention. Certain side chains may contain more than one chiral center. In these cases the diastereoisomers may be separated and utilized individually. All such mixtures and separated mixtures are contemplated by the invention.

A novel process of this invention is for preparing compounds of formula I

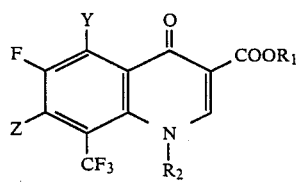

which comprises
(a) carboxylating 1-bromo-2,4,5-trifluorobenzene forming 3-bromo-2,5,6-trifluorobenzoic acid,
(b) fluorinating the carboxylic acid group of the above compound forming 1-bromo-2,4,5-trifluoro-3-(trifluoromethyl)benzene,
(c) carboxylating the bromine position on the above compound forming 2,4,5-trifluoro-3-(trifluoromethyl)benzoic acid,
(d) reacting the above benzoic acid compound with a chlorinating agent, an alkyl hydrogen malonate, and n-butyl lithium forming an alkyl 2,4,5-trifluoro-β-oxo-3-(trifluoromethyl)benzenepropanoate product,
(e) reacting the above product with alkyl orthoformate and acetic anhydride and then with a primary alkyl amine forming alkyl α-(N-alkylaminomethylene)-2,4,5-trifluoro-β-oxo-3-(trifluoromethyl)benzenepropanoate,
(f) cyclizing the above compound by reacting it with a base in a solvent forming alkyl 1-alkyl-6,7-difluoro-1,4-dihydro-4-oxo-8-(trifluoromethyl)-3-quinolinecarboxylate,
(g) deesterifying the above carboxylate forming the corresponding carboxylic acid, and
(h) reacting the above carboxylic acid with a secondary amine to form a compound of formula I and convert, if desired, to a pharamceutically acceptable acid addition or base salt thereof.

The following secondary amines may be used in step h above to form a compound of formula I which may be converted, if desired, to a pharamceutically acceptable acid addition or base salt thereof:

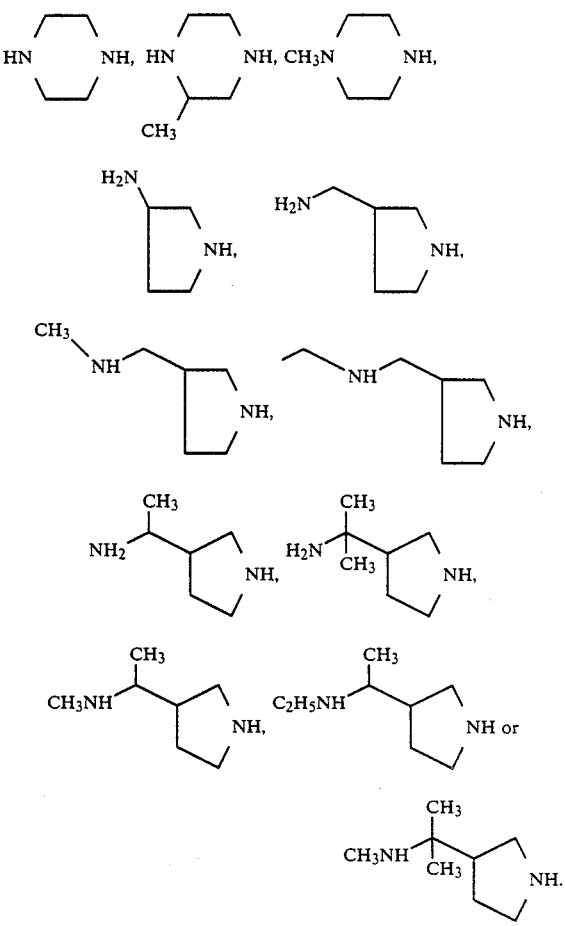

The process is illustrated but not limited by Scheme I below.

Scheme I

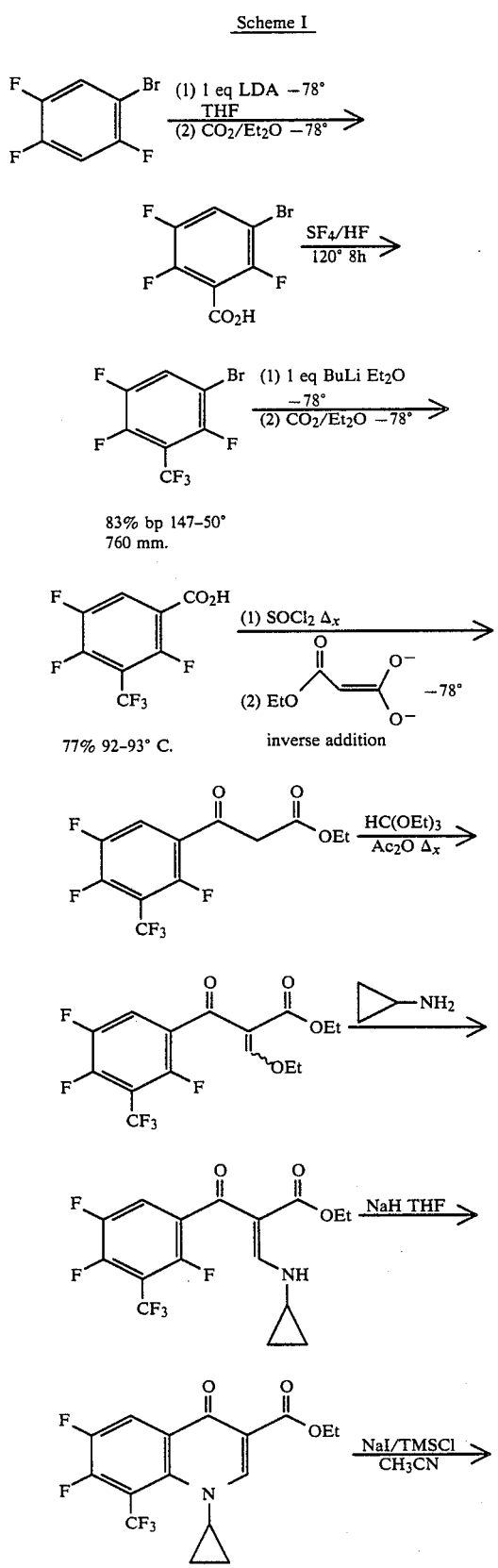

-continued
Scheme I

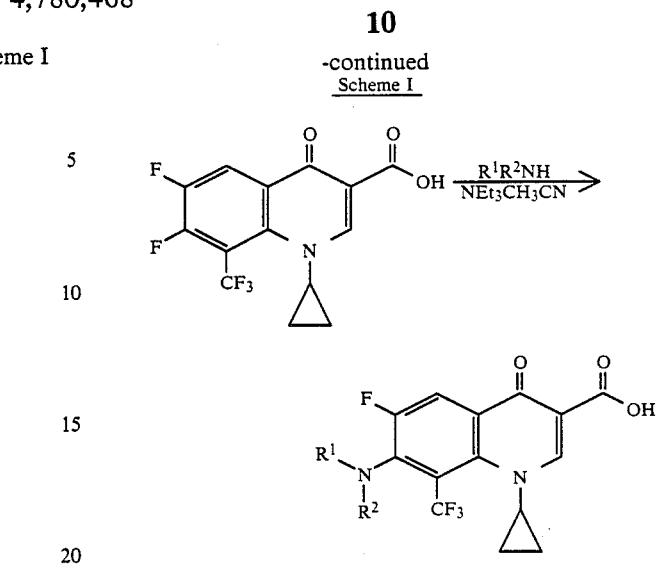

A novel process of the instant invention comprises lithiating and subsequently carboxylating 2,4,5-trifluorobromobenzene (Aldrich) to form the compound 3-bromo-2,5,6-trifluorobenzoic acid. Various lithiating agents such as a lithium dialkylamide, for example lithium diisopropylamide, and carbon dioxide in diethyl ether may be used. The reaction proceeds at temperatures from about −40° to −100° C., preferably from about −60° to −80° C. Possible solvents include but are not limited to ether, dimethoxy ethane and tetrahydrofuran. The preferred solvent is tetrahydrofuran.

The carboxylic acid group of the 3-bromo-2,5,6-trifluorobenzoic acid is treated with a fluorinating agent such as, for example, selenium tetrafluoride or sulphur tetrafluoride and hydrogen fluoride forming the compound 1-bromo-2,4,5-trifluoro-3-(trifluoromethyl)benzene. The reaction proceeds for from about one to forty-eight hours at temperatures of about 80° to 150° C. Preferably the reaction time is from about six to eight hours at temperatures from about 120° to 140° C.

Subsequently the bromine group of the above compound is treated with a carboxylating agent forming the compound 2,4,5-trifluoro-3- (trifluoromethyl)benzoic acid. Possible carboxylating agents include but are not limited by n-butyl lithium and carbon dioxide, Mg and either $CO_2$ or a chloroformate followed by ester hydrolysis, or other organolithium such as MeLi or t-butyl followed by an anhydrous halide salt of a less electropositive metal, then followed either by $CO_2$ or a chloroformate derivative, which would be subsequently hydrolysed; preferably n-butyl lithium and carbon dioxide are used. This portion of the process proceeds at temperatures from about −40° to −100° C. in ether or tetrahydrofuran. Temperatures from about −70° to −80° are preferred. Alternatively, displacement of bromine by CuCN/DMF at 60°-140° C., followed by hydrolysis in strong acid.

The benzoic acid formed above is then treated with a chlorinating agent, an alkyl hydrogen malonate and n-butyl lithium forming the desired alkyl 2,4,5-trifluoro-β-oxo-3-(trifluoromethyl)benzenepropanoate. Various chlorinating agents will be useful such as, for example thionyl chloride, $POCl_3$, $PCl_3$, and $PCl_5$. Brominating agents are also possible such as, for example, $SOBr_2$. Thionyl chloride is the preferred agent used with a dianion of a malonate, such as ethyl hydrogen malonate. The reaction proceeds at temperatures of from about −40° to −100° C.; preferably from about −70° to −85° C.

The above propanoate is reacted with an alkyl orthoformate and acetic anhydride and subsequently with a primary alkylamino forming an ethyl (N-(cyclo)alkylaminomethylene)-3-oxo-3-aryl propanoate derivative (5b). The reactants are preferably ethyl orthoformate and cyclopropylamine or ethylamine. The reaction proceeds for about one to six hours at reflux.

The above seco quinolone product was reacted with a base in an organic solvent to cyclize the compound forming alkyl N-alkyl-6,7-difluoro-8-trifluoromethyl-quinol-4-one-3-carboxylate. A preferred base is an alkali hydride such as sodium hydride or tertiary amine such as triethylamine and solvents includes but are not limited to t-butanol, DMSO, tetrahydrofuran. The reaction occurs at temperatures from about −20° to 100° C.

The quinoline is then deesterified forming the corresponding carboxylic acid. Useful reactants are chlorotrimethylsilane and sodium iodide in acetonitrile. Hydrogen chloride in acetic acid is also useful. The deesterification occurs at reflux which in the case of acetonitrile would be at about 80° C. The reaction time is from two to six hours.

The resulting quinolone is reacted with a secondary amine forming a desired compound of the present invention and converting it, if desired, to a pharmaceutically acceptable acid addition or base salt thereof. Possible reaction solvents include acetonitrile, DMSO, or DMF. The reaction proceeds at between 0° and 100° for from about two to ten hours. Secondary amines reacted with the compound may be protected as necessary. Possible secondary amines include but are not limited to all the secondary amines described herein by Z.

The compounds of the invention can be prepared and administered in a wide variety of oral, parenteral and topical dosage forms. It will be obvious to those skilled in the art that the following dosage forms may comprise as the active component, either a compound of formula I or a corresponding pharmaceutically acceptable salt of a compound of formula I.

For preparing pharmaceutical compositions from the compounds described by this invention, inert, pharmaceutically acceptable carriers can be either solid or liquid. Solid form preparations include powders, tablets, dispersible granules, capsules, cachets, suppositories, and ointments. A solid carrier can be one or more substances which may also act as diluents, flavoring agents, solubilizers, lubricants, suspending agents, binders, or tablet disintegrating agents; it can also be an encapsulating material. In powders, the carrier is a finely divided solid which is in admixture with the finely divided active compound. In the tablet the active compound is mixed with carrier having the necessary binding properties in suitable proportions and compacted in the shape and size desired. The powders and tablets preferably contain from 5 or 10 to about 70 percent of the active ingredient. Suitable solid carriers are magnesium carbonate, magnesium sterate, talc, sugar, lactose, pectin, dextrin, starch, gelatin, tragacanth, methyl cellulose, sodium carboxymethyl cellulose, a low melting wax, cocoa butter, and the like. The term "preparation" is intended to include the formulation of the active compound with encapsulating material as carrier providing a capsule in which the active component (with or without other carriers) is surrounded by carrier, which is thus in association with it. Similarly, cachets are included. Tablets, powders, cachets, and capsules can be used as solid dosage forms suitable for oral administration.

Liquid form preparations include solutions, suspensions and emulsions. As an example may be mentioned water or water-propylene glycol solutions for parenteral injection. Such solutions are prepared so as to be acceptable to biological systems (isotonicity, pH, etc). Liquid preparations can also be formulated in solution in aqueous polyethylene glycol solution. Aqueous solutions suitable for oral use can be prepared by dissolving the active component in water and adding suitable colorants, flavors, stabilizing, and thickening agents as desired. Aqueous suspension suitable for oral use can be made by dispersing the finely divided active component in water with viscous material, i.e., natural or synthetic gums, resins, methyl cellulose, sodium carboxymethyl cellulose, and other well-known suspending agents.

Ointment preparations contain heavy metal salts of a compound of formula I with a physiologically acceptable carrier. The carrier is desirably a conventional water-dispersible hydrophilic or oil-in-water carrier, particularly a conventional semi-soft or cream-like water-dispersible or water soluble, oil-in-water emulsion which may be applied to an affected burn surface or infected surface with a minimum of discomfort. Suitable compositions may be prepared by merely incorporating or homogeneously admixing finely divided compounds with the hydrophilic carrier or base or ointment.

Preferably, the pharmaceutical preparation is in unit dosage form. In such form, the preparation is subdivided into unit doses containing appropriate quantities of the active component. The unit dosage form can be a packaged preparation, the package containing discrete quantities of preparation, for example, packeted tablets, capsules, powders in vials or ampules, and ointments in tubes or jars. The unit dosage form can also be a capsule, cachet, tablet, gel or cream itself or it can be the appropriate number of any of these packaged forms.

The quantity of active compound in a unit dose of preparation may be varied or adjusted from 1 mg to 100 mg according to the particular application and the potency of the active ingredient.

In therapeutic use as agents for treating bacterial infections the compounds utilized in the pharmaceutical method of this invention are administered at the initial dosage of about 3 mg to about 40 mg per kilogram daily. A daily dose range of about 6 mg to about 14 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate methods for preparing the compounds of the invention.

EXAMPLE 1

3-Bromo-2,5,6-trifluorobenzoic acid n-Butyl lithium (2.6M in hexanes, 32 mL, 84 mmol) was added over 10 minutes to a solution of diisopropylamine (8.89 g, 88 mmol) in THF (80 mL) stirred under N₂ at 0° C. After a further 10 minutes at 0°, the solution was transferred by catheter over 40 minutes to a solution of 2,4,5-trifluorobromobenzene (16.88 g, 80 mmol) in THF (200 mL) stirred under N₂ at −78°. After a further 15 minutes the solution was blown through a catheter over ≈2 minutes onto a slurry of CO₂ (≈200 mL) in ether (400 mL) with vigorous stirring. When the CO₂ evaporated the slurry was washed with dilute HCl (1M, 200 mL) and water (100 mL). The organic phase was extracted with dilute NaOH (0.5M, 2×100 mL). The aqueous phase was washed with ether (100 mL) and made acidic (12N HCl, 9 mL). The aqueous phase was extracted with ether (2×100 mL), and the combined organic phases were washed with water (100 mL), saturated brine (100 mL) and dried (MgSO₄) The solvent was removed under reduced pressure to give 3-bromo-2,5,6-trifluorobenzoic acid (17.25 g, 84.5%) as white microcrystalline needles; mp 114°–6° (sublimation). Nmr (CDCl₃) δ 10.73 (1H, s, OH), 7.54 (1H, d of t, $J_d$=6 Hz, $J_t$=9 Hz aromatic).

EXAMPLE 2

1-Bromo-2,4,5-trifluoro-3-(trifluoromethyl)benzene

3-Bromo-2,5,6-trifluorobenzoic acid (16.92 g, 66 mmol) was heated with SF₄ (60 g) and HF (30 g) in a stainless steel bomb at 120° for 8 hours. When the reaction cooled to 25° the volatiles were vented through KOH traps, and when gas evolution ceased the vessel was extracted with CH₂Cl₂ (150 mL). This solution was washed with diluted NaHCO₃ solution (saturated/2, 50 mL), saturated brine (50 mL), and dried (MgSO₄). The solvent was removed by distillation through a 15 cm Vigreux column, and the residue was distilled under N₂ through a shortpath stillhead at 147°–150° to give 1-bromo-2,4,5-trifluoro-3-(trifluoromethyl)benzene (15.79 g, 83%) as a pale yellow oil. Nmr (CDCl₃) δ 7.67 (1H, d of t, $J_d$=6 Hz, $J_t$=8.1 Hz, aromatic). Ir (film) 1495, 1315, 1211, 1165, 1149, 919. M.S. 280 (97 $^{81}$BrM⊕), 278 (100, $^{79}$BrM⊕).

EXAMPLE 3

2,4,5-Trifluoro-3-(trifluoromethyl)benzoic acid

A solution of n-butyl lithium (2.6M in hexanes, 9.6 mL, 25 mmol) was added dropwise through an addition funnel over 15 minutes to a solution of 1-bromo-2,4,5-trifluoro-3-(trifluoromethyl)benzene (7.00 g, 25 mmol) in ether (100 mL) stirred under N₂ at −78°. After 5 minutes the rxn mixture was rapidly blown by catheter onto a suspension of dry ice (100 g) in ether (100 mL). After 5 minutes TFA (2 mL) was added to this. When the solution had warmed up to 20° C., it was washed with diluted HCl (0.5M, 20 mL), and extracted with dilute base (0.5N, 2×50 mL). The combined basic extracts were washed with ether (25 mL), made acidic with concentrated HCl (≈4 mL) and extracted with ether (3×50 mL). The combined ethereal extracts were washed with water (50 mL), saturated brine (50 mL) and dried (MgSO₄). The solvent was removed under reduced pressure to give 2,4,5-trifluoro-3-(trifluoromethyl)benzoic acid (4.21 g, 69%) as white microscopic needles; mp 87°–90° C. Nmr (CDCl₃) δ 11.80 (1H, br s, OH), 8.05 (1H, d of t, $J_d$=6 Hz, $J_t$=9 Hz, aromatic). IR (KBr) 1721, 1636, 1511, 1464, 1424, 1328, 1256, 1154, 928 cm⁻¹. M⊕ 244 (56).

EXAMPLE 4

Ethyl 2,4,5-trifluoro-β-oxo-3-(trifluoromethyl)benzenepropanoate 2,4,5-Trifluoro-3-(trifluoromethyl)benzoic acid (0.49 g, 2 mmol) was refluxed in SOCl₂ (1 mL) under N₂ for 2½ hours. The volatiles were removed under reduced pressure, and azeotroped further with toluene (5 mL). The residual light yellow-brown oil was dissolved in THF (5 mL), and cooled to −78° under N₂ with stirring.

n-Butyl lithium (3.1 mL, 8 mmol, 2.6M in hexanes) was added dropwise to a solution of ethyl hydrogen malonate (0.53 g, 4 mmol) and bipyridyl (1 mg) in THF (5 mL) stirred at −78° under N₂, until pink coloration (≈1.5 mL). The reaction mixture was stirred on an ice salt bath and the remainder of the butyl lithium was added, giving a pink color. This suspension was then added dropwise via syringe over 10 minutes to the −78° solution of the acid chloride, to form a nearly clear bright yellow solution. After 2 hours at −78° the rxn mixture was quenched by rapid addition of dilute HCl (1M, 8 mL). When the mixture had melted, it was poured onto water (25 mL), and extracted with ether (3×10 mL). The combined organic extracts were washed wtih water (10 mL), saturated NaHCO₃ (10 mL), saturated brine (10 mL) and dried (MgSO₄) The solvent was removed under reduced pressure to give ethyl-3-oxo-3-(2,4,5-trifluoro-3-(trifluoromethyl)-phenyl)propanoate (0.52 g, 83%) as a golden-brown oil. Nmr (CDCl₃) δ 7.91 (1H, sl br, d of t, $J_d$=6 Hz, $J_t$=9 Hz, aromatic), 5.74 (≈⅓H, br s, vinyl of enol), 4.15 (2H, q, J=7 Hz, OCH₂), 3.90 (≈1⅓H, d, J=4 Hz, methylene α to CO), 1.1–1.5 (≈4H, 2 overlapping t+broad m, CH₃s), 0.7–1.0 (≈1H, m, Bu n related).

EXAMPLE 5

Ethyl 1-cyclopropyl-6,7-difluoro-1,4-dihydro-4-oxo-8-(trifluoromethyl)-3-quinolinecarboxylate Ethyl 2,4,5-trifluoro-β-oxo-3-(trifluoromethyl)benzenepropanoate (0.52 g, 1.67 mmol) ethyl orthoformate (0.45 g, 3 mmol) and acetic anhydride (0.41 g, 4 mmol) were refluxed under N₂ for 90 minutes. The volatiles were removed under reduced pressure, and the residual brown oil (0.59 g) was mixed with cyclopropylamine (0.12 g, 2 mmol) in THF (5 mL) stirred under N₂ at 20° C. After 90 minutes the volatiles were removed under reduced pressure to give a waxy brown solid. This was dissolved in THF (5 mL) under N₂ at 20° with stirring, and sodium hydride (60% oil suspension, 0.10 g, 2.5 mmol) was added. After 15 minutes the reaction was quenched by addition of acetic acid (1 mL). The reaction mixture was diluted with CHCl₃ (25 mL) and washed with water (2×25 mL) and dried (MgSO₄). The solvent was removed under reduced pressure to give a reddish-brown solid, which was purified by preparative tlc on silica (2×20 cm) eluting with 5% MeOH in CHCl₃. The major band ($r_f$=0.66) was extracted with CHCl₃/MeOH, and the solvent was removed under reduced pressure to give ethyl N-cyclopropyl-6,7-difluoro-8-trifluoromethyl-quinol-4-one-3-carboxylate (0.14 g, 23%) as an ochre solid; mp 174°–9° C. Nmr (CDCl₃) δ 8.68 (1H, s, H2), 8.42 (1H, t, J=9 Hz, H5), 4.40 (2H, q, J=6.1 Hz, OCH₂), 3.92–4.07 (1H, m, NCH), 1.41 (3H, t, J=6.1 Hz, CH₃), 1.15–1.25 (2H, m, cyclopropyl), 0.67–0.75 (2H, m, cyclopropyl). Ir (KBr) 1738, 1638, 1612, 1470, 1311, 1297, 1269, 1190, 1180, 1162, 1151, 1074, 897, 805. $M^\oplus$ 361 (10).

EXAMPLE 6

1-Cyclopropyl-6,7-difluoro-1,4-dihydro-4-oxo-8-(trifluoromethyl)-3-quinolinecarboxylic acid Chlorotrimethylsilane (0.54 g, 5 mmol) ethyl 1-cyclopropyl-6,7-difluoro-1,4-dihydro-4-oxo-8-(trifluorophenyl)-3-quinolinecarboxylate (0.76 g, 2.1 mmol) and NaI (0.75 g, 5 mmol) were stirred in refluxing CH$_3$CN (10 mL) under N$_2$ for 8 hours. On cooling water (30 mL) was added and the mixture was extracted with EtOAc (2×20 mL). The combined extracts were washed with water (2×10 mL), saturated brine (12 mL), and dried (MgSO$_4$). The solvent was removed under reduced pressure, and the residual brown solid (0.74 g) was dissolved in hot CHCl$_3$, and precipitated with ether at 0° C. to give 1-cyclopropyl-6,7-difluoro-1,4-dihydro-4-oxo-8-(trifluoromethyl)-3-quinolinecarboxylic acid (0.43 g, 62%) as yellow needles; mp 243.5°–244.5° C. C$_{14}$H$_8$F$_5$NO$_3$ requires C, 50.45; H, 2.40 N, 4.20 F, 28.53%. Found C, 50.10; H, 2.27; N, 4.03 F, 28.08%. Nmr (DMSO) δ 13.5–14.5 (1H, br s, OH), 8.98 (1H, s, H2), 8.53 (1H, t, J=9.2 Hz, H5), 4.15–4.25 (1H, m, NCH), 1.05–1.15 (2H, m, CH$_2$), 0.80–0.88 (2H, m, CH$_2$) Ir (KBr) 1724, 1630, 1618, 1565, 1505, 1467, 1429, 1398, 1337, 1324, 1283, 1269, 1199, 1180, 1172, 1161, 1130, 1093, 1051, 1023, 922, 910, 808, 743 cm$^{-1}$. MS 334 (5 MH+) 333 (13, M+).

EXAMPLE 7

1-Cyclopropyl-7-(3-((N-ethylamino)methyl)-1-pyrrolidinvl)-6-fluoro-1,4-dihydro-4-oxo-8-(trifluoromethyl)-3-quinolinecarboxylic acid 1-Cyclopropyl-6,7-difluoro-1,4-dihydro-4-oxo-8-(trifluoromethyl)-3-quinolinecarboxylic acid (0.20 g, 0.61 mmol) 3-((N-ethylamino)methyl)pyrrolidine (0.20 g, 1.6 mmol) and NEt$_3$ (0.20 g, 2 mmol) were refluxed with stirring under N$_2$ in CH$_3$CN (2 mL) for 2 hours. When the reaction mixture had cooled to 20° the yellow solid was collected by vacuum filtration, washed with water (5 mL) and ether (5 mL), and then dried at 110°/0.2 mm to give 1-cyclopropyl-7-(3-((N-ethylamino)methyl)pyrrolidinyl)-6-fluoro-1,4-dihydro-4-oxo-8-(trifluoromethyl)-3-quinolinecarboxylic acid (0.26 g, 97%) as a light yellow solid; mp 239°–241° C. C$_{21}$H$_{23}$N$_3$O$_3$F$_4$ requires C, 57.14; H, 5.22; N, 9.52; F, 17.23%. Found, C, 56.77; H, 4.98; N, 9.34; F, 16.95%. Nmr (TFA) δ 9.37 (1H, s, H2), 8.09 (1H, d, J=13.8 Hz, H5), 7.2–7.5 (2H, br s, NH+$_2$), 4.45–4.55 (1H, m, H1 pyrrolidinyl), 4.1–4.4 (2H, m, H5 pyrrolidinyl), 3.9–4.1 (2H, m, H1 cyclopropyl+pyrrolidinyl), 3.3–3.65 (4H, m, CH$_{2s}$ ethylaminomethyl), 2.9–3.1 (1H, m, H3 pyrrolidinyl), 2.5–2.65 (1H, m, H4 pyrrolidinyl), 1.9–2.1 (1H, m, H4 pyrrolidinyl), 1.5–1.8 (5H, m and t, J=7.1 Hz, cyclopropyl and CH$_3$), 0.95–1.4 (2H, m, cyclopropyls). Ir (KBr) 1629, 1456, 1360 cm$^{-1}$. MS 442 (4, M H$^\oplus$), 441 (4, M$^\oplus$).

We claim:

1. A compound of the formula

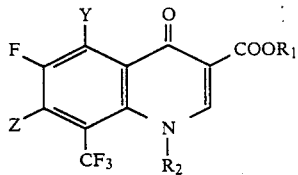

wherein

R$_1$ is hydrogen, an alkyl of from one to six carbon atoms or a cation;

R$_2$ is alkyl of from one to four carbon atoms, vinyl, haloalkyl or hydroxyalkyl of from one to four carbon atoms or cycloalkyl of from three to six carbon atoms;

Y is hydrogen, fluoro, or amino;

Z is

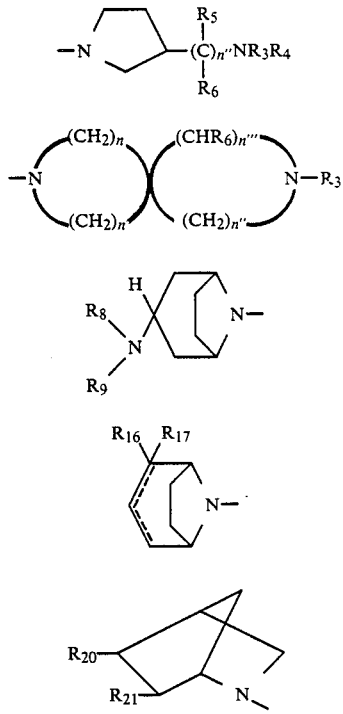

wherein n is 1, 2, 3, or 4;

n' is 1, 2, 3, or 4;

n+n' is a total of 2, 3, 4, or 5;

n" is 0, 1, or 2;

n''' is 0, 1, or 2;

n$^{lv}$ is 1, 2, or 3;

n$^v$ is 0 or 1;

R$_3$ is hydrogen, alkyl of from one or four carbon atoms or a cycloalkyl of from three to six carbon atoms;

R$_4$ is hydrogen, alkyl of from one to four carbon atoms, hydroxyalkyl of from two to four carbon atoms, trifluoroethyl, or R$_4$'CO wherein R$_4$' is alkyl of from one to four carbon atoms, or alkoxy of from one to four carbon atoms;

R$_5$ and R$_6$ are each independently hydrogen or alkyl of from one to three carbon atoms;

R₇ is hydrogen, alkyl of from one to three carbon atoms, hydroxyalkyl of from two to three carbon atoms, benzyl, or p-aminobenzyl;

R₈ and R₉ are each independently hydrogen, alkanoyl of from one to three carbon atoms, alkyl of from one to three carbon atoms, isopropyl or cyclopropyl;

R₁₀ and R₁₁ are each independently hydrogen, methyl, ethyl, or benzyl;

R₁₂, R₁₃, and R₁₄ are each independently hydrogen or methyl;

R₁₅ is methyl, ethyl, or isopropyl;

R₁₆ is CH₂OR₁₈, CH₂NR₁₈R₁₉, or NR₁₈R₁₉ wherein R₁₈ and R₁₉ are hydrogen, alkyl of from one to three carbon atoms, alkanoyl of from one to three carbon atoms;

R₁₇ is absent, hydrogen or alkyl of from one to three carbon atoms;

wherein the dotted line means a single or double bond;

R₂₀ and R₂₁ are each independently hydrogen, halogen, NR₂₂R₂₃, OR₂₂, SR₂₂, alkyl of from one to three carbon atoms, wherein R₂₂ and R₂₃ are each independently hydrogen, alkyl of from one to three carbon atoms, or acyl of from one to three carbon atoms;

or a pharmaceutically acceptable acid addition or base salt thereof.

2. A compound according to claim 1 wherein R₂ is ethyl, vinyl, 2-fluoroethyl, difluoroethyl, or cyclopropyl.

3. A compound according to claim 1 where Z is

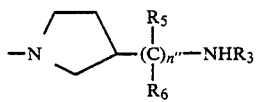

or

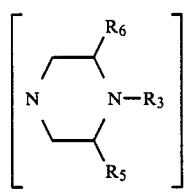

wherein R₃ is hydrogen, methyl, ethyl, n-propyl, or 2-propyl, R₅ and R₆ are hydrogen, methyl, or ethyl and n'' is 0 or 1.

4. A compound according to claim 1 wherein R is hydrogen or a pharmaceutically acceptable base salt thereof.

5. A compound according to claim 1 and being 7-(3-(aminomethyl)pyrrolidin-1-yl)-1-ethyl-6-fluoro-8-(trifluoromethyl)-1,4-dihydro-4-oxoquinoline-3-carboxylic acid.

6. A compound according to claim 1 and being 7-[3-(1-aminoethyl)-1-pyrrolidinyl]-1-cyclopropyl-6-fluoro-1,4-dihydro-4-oxo-8-(trifluoromethyl)-3-quinolinecarboxylic acid.

7. A compound according to claim 1 and being 1-cyclopropyl-7-[3-[1-(ethylamino)ethyl]-1-pyrrolidinyl]-6-fluoro-1,4-dihydro-4-oxo-8-(trifluoromethyl)-3-quinolinecarboxylic acid.

8. A compound according to claim 1 and being 1-cyclopropyl-6-fluoro-1,4-dihydro-7-[3-[1-methyl-1-(methylamino)ethyl]-1-pyrrolidinyl]-4-oxo-8-(trifluoromethyl)-3-quinolinecarboxylic acid.

9. A compound according to claim 1 and being 7-[3-(aminomethyl)-1-pyrrolidinyl]-1-cyclopropyl-6-fluoro-1,4-dihydro-4-oxo-8-(trifluoromethyl)-3-quinolinecarboxylic acid.

10. A compound according to claim 1 and being 1-ethyl-6-fluoro-1,4-dihydro-7-[3-[(methylamino)methyl]-1-pyrrolidinyl]-4-oxo-8-(trifluoromethyl)-3-quinolinecarboxylic acid.

11. A compound according to claim 1 and being 1-cyclopropyl-6-fluoro-1,4-dihydro-7-[3-[(methylamino)methyl]-1-pyrrolidinyl]-4-oxo-8-(trifluoromethyl)-3-quinolinecarboxylic acid.

12. A compound according to claim 1 and being 1-ethyl-7-[3-[(ethylamino)methyl]-1-pyrrolidinyl]-6-fluoro-1,4-dihydro-4-oxo-8-(trifluoromethyl)-3-quinolinecarboxylic acid.

13. A compound according to claim 1 and being 1-cyclopropyl-7-3-(ethylamino)methyl]-1-pyrrolidinyl]-6-fluoro-1,4-dihydro-4-oxo-8-(trifluoromethyl)-3-quinolinecarboxylic acid.

14. A compound according to claim 1 and being 7-(3-amino-1-pyrrolidinyl)-1-ethyl-6-fluoro-1,4-dihydro-4-oxo-8-(trifluoromethyl)-3-quinolinecarboxylic acid.

15. A compound according to claim 1 and being 7-(3-amino-1-pyrrolidinyl)-1-cyclopropyl-6-fluoro-1,4-dihydro-4-oxo-8-(trifluoromethyl)-3-quinolinecarboxylic acid.

16. A compound according to claim 1 and being 7-[3-(1-amino-1-methylethyl)-1-pyrrolidinyl]-1-cyclopropyl-6-fluoro-1,4-dihydro-4-oxo-8-(trifluoromethyl)-3-quinolinecarboxylic acid.

17. A pharmaceutical composition comprising an antibacterially effective amount of a compound as claimed in claim 1 together with a pharmaceutically acceptable carrier.

18. A method of treating bacterial infections in mammals which comprises administering to said mammal a pharmaceutical composition as claimed in claim 17 in unit dosage form.

* * * * *

UNITED STATES PATENT AND TRADEMARK OFFICE
CERTIFICATE OF CORRECTION

PATENT NO. : 4,780,468

DATED : October 25, 1988

INVENTOR(S) : ALEXANDER BRIDGES and JOHN M. DOMAGALA

It is certified that error appears in the above—identified patent and that said Letters Patent is hereby corrected as shown below:

In Column 16, line 30, delete " 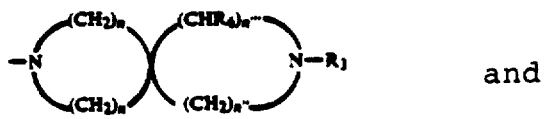 " and insert -- 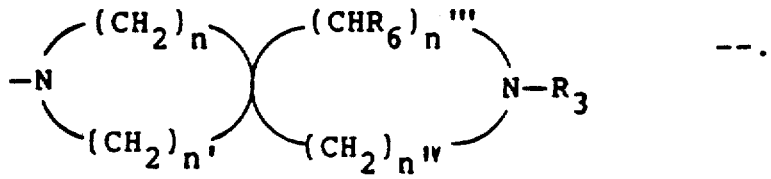 --.

Column 18, line 34, "cyclopropyl-7-3-" should read -- cyclopropyl-7-[3- --.

UNITED STATES PATENT AND TRADEMARK OFFICE
CERTIFICATE OF CORRECTION

Page 2 of 2

PATENT NO. : 4,780,468
DATED : October 25, 1988
INVENTOR(S) : ALEXANDER J. BRIDGES and JOHN M. DOMAGALA It is certified that error appears in the above—identified patent and that said Letters Patent is hereby corrected as shown below:

Column 16, line 58, delete "$n^V$ is 0 or 1;".

Column 17, delete lines 1-3.

Column 17, delete lines 8-12.

Signed and Sealed this

Twenty-first Day of March, 1989

Attest:

DONALD J. QUIGG

*Attesting Officer*  *Commissioner of Patents and Trademarks*